United States Patent [19]

Fischer

[11] Patent Number: 5,627,291

[45] Date of Patent: May 6, 1997

[54] PREPARATION OF 2,5-DIHYDROFURAN

[75] Inventor: Martin Fischer, Ludwigshafen, Germany

[73] Assignee: BASF Aktiengesellschaft, Ludwigshafen, Germany

[21] Appl. No.: 498,973

[22] Filed: Jul. 6, 1995

[30] Foreign Application Priority Data

Jul. 9, 1994 [DE] Germany .................... 44 24 219.0

[51] Int. Cl.$^6$ .................................................. C07D 307/02
[52] U.S. Cl. ........................................................ 549/507
[58] Field of Search .......................................... 549/507

[56] References Cited

U.S. PATENT DOCUMENTS

| | | | |
|---|---|---|---|
| 3,812,158 | 5/1974 | Besozzi et al. | 260/346.1 R |
| 3,996,248 | 12/1976 | Wall et al. | 260/346.1 R |
| 5,034,545 | 7/1991 | Fischer | 549/507 |
| 5,238,889 | 8/1993 | Falling et al. | 502/24 |

FOREIGN PATENT DOCUMENTS

| | | |
|---|---|---|
| 412366 | 2/1991 | European Pat. Off. . |
| 91/13882 | 9/1991 | WIPO . |
| 93/10111 | 5/1993 | WIPO . |

OTHER PUBLICATIONS

Gevorkyan et al., *Zh. Org. Khim.*, 1988, 24(6), pp. 1340-1341 (submitted in English as translated in *J. Org. Chem. USSR*, 1207, 1988).

*Chem. Abst.*, vol. 110, No. 9, abstract No. 75197t 1989.

*Primary Examiner*—Amelia Owens
*Attorney, Agent, or Firm*—Keil & Weinkauf

[57] ABSTRACT

A process for the preparation of 2,5-dihydrofurans of the general formula I

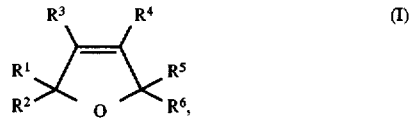

in which the radicals $R^1$, $R^2$, $R^3$, $R^4$, $R^5$, and $R^6$ are the same or different and stand for hydrogen or $C_1$–$C_4$ alkyl groups, by the catalytic rearrangement of 3,4-epoxy-1-butenes of the general formula II

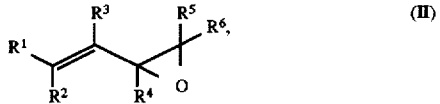

in the presence of a Lewis acid or elementary iodine and in the presence or absence of an organic solubilizing agent at a temperature of from 60° to 200° C., wherein the reaction is carried out in the presence of a phosphazenium halide or a phosphazanium halide or in the presence of mixtures of phosphazenium and phosphazanium halides.

18 Claims, No Drawings

PREPARATION OF 2,5-DIHYDROFURAN

The present invention relates to a process for the preparation of 2,5-dihydrofurans of the general formula I

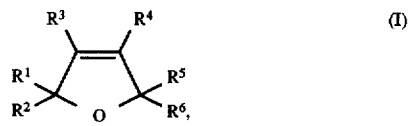 (I)

in which the radicals $R^1$, $R^2$, $R^3$, $R^4$, $R^5$, and $R^6$ are the same or different and stand for hydrogen or $C_1$–$C_4$ alkyl groups, by the catalytic rearrangement of 3,4-epoxy-1-butenes of the general formula II

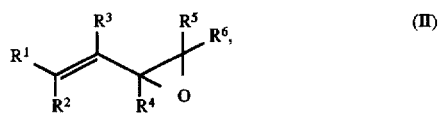 (II)

in the presence of a Lewis acid or elementary iodine and in the presence or absence of a solubilizing agent at a temperature of from 60° to 200° C.

2,5-Dihydrofuran can be obtained, according to U.S. Pat. No. 3,812,158, by the isomerization of vinyl oxirane under the action of mercury salts. Apart from the fact that in this process 2,5-dihydrofuran can be isolated only in a maximum yield of 33%, the use of the toxic mercury salt catalysts is an obstacle to the industrial utilization of this process.

U.S. Pat. No. 3,932,468 describes the chemical rearrangement of butadiene monoxide to produce 2,5-dihydrofuran, this being catalyzed by transition metal complexes and hydrogen bromide gas or hydrogen iodide gas. U.S. Pat. No. 3,996,248 also requires hydrogen bromide or hydrogen iodide for this rearrangement. According to said patent, to improve the hydrogen halide catalysis, Lewis acids homogeneously dissolved in the reaction medium, such as zinc, aluminum, boron, tin, or magnesium compounds, are used. Furthermore, potassium iodide is added to the reaction system.

A drawback of these two processes is that due to the presence of hydrogen halides in the reaction medium during the isolation, by distillation, of 2,5-dihydrofuran, considerable losses occur and the dihydrofuran obtained is contaminated by hydrogen halide and/or iodine. Thus the yield of 2,5-dihydrofuran drops, according to the statements of U.S. Pat. No. 3,932,468, from 78% in the crude product (determined by gas chromatography) to 58% following distillation of the product, whilst the distillate has a dihydrofuran content of only 89%. This process is therefore uneconomical.

Further reasons for the uneconomical performance of these processes are the corrosion problems which are caused by the use of hydrogen halide catalysts, and the high consumption of solvents and catalysts, which cannot be recycled.

WO 91/13882 describes a gas phase process for the isomerization of epoxy alkenes to produce 2,5-dihydrofurans. Mixtures of ammonium iodides or phosphonium iodides and Lewis acids on a support material serve as catalysts. Since onium halides gradually decompose at temperatures above 130° C. and the epoxide gradually forms high-boiling oligomers and polymers during the reaction, which become deposited on the surface of the catalyst and thus block it, the activity of the catalyst and thus the conversion of the epoxide considerably decreases after a short on-stream period, so that this process is uneconomical.

Furthermore, the isomerization of epoxy alkenes in the liquid phase is described in WO 91/13882, in which the Lewis acids used comprise organotin or organo-antimony compounds in combination with a tetraalkylammonium iodide or a phosphonium iodide. The same type of catalyst is used in WO 93/1 0111 and U.S. Pat. No. 5,238,889.

As early as EP-A 412,366 we have a report on a process for the isomerization of epoxy alkenes to produce 2,5-dihydrofurans in the liquid phase, in which process a Lewis acid was used in the presence of an alkali metal iodide or onium iodide or elementary iodine in the presence or absence of a solubilizing agent acting as catalyst. The best results were achieved in this process using the combination zinc halide/alkali metal halide.

Although the last-named liquid phase processes yield good yields of 2,5-dihydrofurans by isomerization of epoxy butenes, they are still in need of improvement. Thus oligomers and polymers of epoxy butene form in the course of the reaction, which particularly hinder the separation of the alkali metal halides and onium halides from the reaction mixture and the recovery of the catalyst. In addition, the alkali metal halides and onium halides must be used in relatively large quantities, in order that satisfactory yields and selectivities can be achieved.

It was thus the object of the present invention to provide a process for the isomerization of epoxy butenes to produce 2,5-dihydrofurans, which is free from the aforementioned drawbacks. A particular object was to find an agent which can assume the function of the alkali metal halides or onium halides in the aforementioned catalyst system with the same or improved performance, but which can be separated from the reaction mixture in a simple manner, in addition, this agent should make it possible to carry out this reaction in the presence of smaller amounts of Lewis acid than is possible in the prior art.

Accordingly, we have found a process for the preparation of 2,5-dihydrofurans of the general formula I

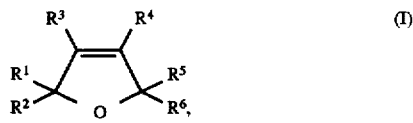 (I)

in which the radicals $R^1$, $R^2$, $R^3$, $R^4$, $R^5$, and $R^6$ are the same or different and stand for hydrogen or $C_1$–$C_4$ alkyl groups, by the catalytic rearrangement of 3,4-epoxy-1-butenes of the general formula II

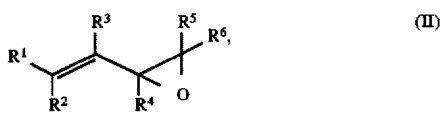 (II)

in the presence of a Lewis acid or elementary iodine and in the presence or absence of an organic solubilizing agent at a temperature of from 60° to 200° C., wherein the reaction is carried out in the presence of a phosphazenium halide or a phosphazanium halide or in the presence of mixtures of phosphazenium and phosphazanium halides.

In the process of the invention such phosphazenium halides or phosphazanium halides are preferably used as are depicted by the general formulas III and IV.

In the phosphazenium halides of the general formula III.

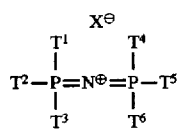

which are also designated as phosphranylideiminium halides, X is the counterion to the positively charged nitrogen atom of the iminium compound III. X is generally a chloride, bromide or iodide ion. The phosphorus atoms of the phosphazenium compound III carry a total of 6 substituents $T^1$, $T^2$, $T^3$, $T^4$, $T^5$, and $T^6$, which can be the same or different and independently stand for optionally substituted $C_1$–$C_{20}$, preferably $C_1$–$C_{10}$ and more preferably $C_1$–$C_6$ alkyl groups, optionally substituted $C_6$–$C_{10}$ aryl groups, preferably the phenyl or naphthyl group, optionally substituted $C_7$–$C_{12}$ aralkyl groups, preferably the benzyl, phenethylene or naphthylmethylene group, di-($C_1$–$C_{10}$ alkyl)amino, preferably di-($C_1$–$C_5$ alkyl)amino groups, particularly the dimethylamino, diethylamino, di-n-propylamino, diisopropylamino, di-n-butyl-amino, di-isobutylamino, di-tert-butylamino, or di-n-pentylamino group or the di-neopentylamino group, di-($C_3$–$C_8$ cycloalkyl)amino groups, preferably di-($C_3$–$C_6$ cycloalkyl)amino groups, particularly dicyclopropyl, dicyclopentylamino, or dicyclohexylamino groups, di-($C_6$–$C_{10}$ aryl)amino groups, preferably the diphenylamino group, ($C_1$–$C_{10}$-alkyl)amino and ($C_6$–$C_{10}$ aryl)amino groups, for example the N-methylanilino group or N-methylnaphthylamino group, di-($C_7$–$C_{12}$ aralkyl)amino groups, such as the dibenzylamino group, ($C_1$–$C_{10}$-alkyl)amino and ($C_7$–$C_{12}$ aralkyl)-amino groups, such as the N,N-methylbenzylamino group, ($C_6$–$C_{10}$-aryl)amino and ($C_7$–$C_{12}$ aralkyl)amino groups, such as the N,N-phenylbenzylamino group, pyrrolidinyl, piperidinyl, morpholinyl oder N'-($C_1$–$C_4$ alkyl)piperazinyl groups.

The substituents $T^1$, $T^2$, $T^3$, $T^4$, $T^5$, and $T^6$ on the phosphorus atoms of the phosphazenium halides III can, particularly if this process involves aliphatic, aromatic, or araliphatic hydrocarbon groups, optionally carry from 1 to 3 further substituents which are inert under the reaction conditions of the process of the invention. Examples of such substituents are $C_1$–$C_{20}$, preferably $C_1$–$C_{10}$ and more preferably $C_1$–$C_4$ alkoxy groups or halogen atoms, particularly chlorine or bromine atoms. The aromatic rings of the aryl or aralkyl substituents can also carry, as substituents, $C_1$–$C_{20}$, preferably $C_1$–$C_{10}$ and more preferably $C_1$–$C_4$ alkyl groups. The substitution pattern and the degree of substitution can usually be chosen arbitrarily, since these substituents generally have no crucial effect on the catalytic performance of the relevant phosphazenium halides III. Consequently such phosphazenium halides III are preferably used in the process of the invention whose alkyl, aryl, or aralkyl-substituents $T^1$, $T^2$, $T^3$, $T^4$, $T^5$, and $T^6$ carry no further substituents. Particularly preferred phosphazenium halides of the general formula III containing optionally substituted hydrocarbon radicals $T^1$, $T^2$, $T^3$, $T^4$, $T^5$, and $T^6$ are those in which these radicals stand for unsubstituted or substituted aryl groups.

The nitrogenous substituents $T^1$, $T^2$, $T^3$, $T^4$, $T^5$, and $T^6$ on the phosphorus atoms, ie, the dialkylamino, dicycloalkylamino, diarylamino, diaralkylamino, alkylarylamino, alkylaralkylamino, or arylaralkylamino groups, the pyrrolidinyl, piperidinyl, morpholinyl groups or N'-($C_1$–$C_4$ alkyl)piperazinyl groups, are linked by the free valency of their nitrogen atom to the individual phosphorus atoms of the phosphazenium compound III.

In each case, the two radicals of the nitrogenous substituents $T^1$, $T^2$, $T^3$, $T^4$, $T^5$, and $T^6$, for example the radicals $T^1$ and $T^2$ or $T^1$ and $T^2$ or $T^4$ and $T^5$ can alternatively, together with the respective phosphorus atom, form a ring, so that, for example, monocyclic or bicyclic phosphazenium salts III are present, as can be represented, for example, by the formula

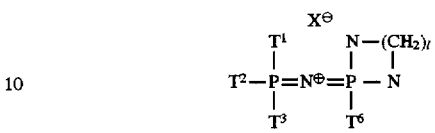

or the formula

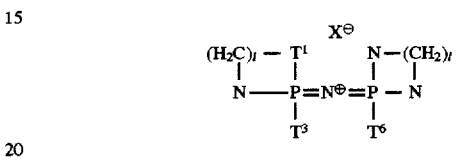

in which l is an integer from 2 to 5, preferably from 3 to 4.

Alternatively, three of the nitrogenous radicals, ie, $T^1$, $T^2$, $T^3$, or $T^4$, $T^5$, $T^6$ can in each case, together with the relevant phosphorus atom, form a bicyclic ring, resulting in phosphazenium salts III of the formula

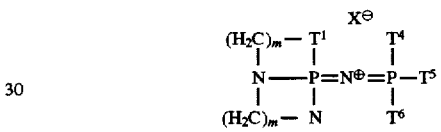

or in which the index m can be the same or different and stands for an integer from 2 to 5, preferably 3 or 4.

Particularly preferred amino group substituents $T^1$, $T^2$, $T^3$, $T^4$, $T^5$, and $T^6$ are di-($C_1$–$C_{10}$ alkyl)amino, particularly di-($C_1$–$C_5$ alkyl)amino groups, such as the dimethylamino, diethylamino, di-n-propylamino, diisopropylamino, di-n-butylamino, diisobutylamino, di-tert-butylamino, di-n-pentylamino, dineopentylamino, methylethylamino, methyl-n-propylamino, methylisopropylamino, methyl-tert-butylamino, methyl-n-butylamino, methylneopentylamino, ethyl-n-propylamino, ethylisopropylamino, ethyl-n-butylamino, ethylisobutylamino, and the ethyl-tert-butylamino groups, furthermore the diphenylamino group, the di-($C_3$–$C_6$ cycloalkyl)amino groups, in particular the dicyclopropyl, dicyclopentyl, and dicyclohexylamino groups and the cycloaliphatic amino groups, in particular the pyrrolidinyl, piperidinyl, morpholinyl, and N'-($C_1$–$C_4$ alkyl) piperazinyl groups.

The radicals $T^1$, $T^2$, $T^3$, $T^4$, $T^5$, and $T^6$ can, as mentioned above, be independently the same or different, ie, in the phosphazenium halides III which can be used in the invention the substituents $T^1$, $T^2$, $T^3$, $T^4$, $T^5$, and $T^6$ can, for example, all be the same and stand for a specific substituent group as defined above, or alternatively, the phosphazenium halides III can contain different substituents $T^1$, $T^2$, $T^3$, $T^4$, $T^5$, and $T^6$ in one molecule, ie a phosphazenium halide of the general formula III which can be used in the invention can have, for example, both hydrocarbon group-containing and amino group-containing substituents $T^1$, $T^2$, $T^3$, $T^4$, $T^5$, and $T^6$. However, it is preferred to use phosphazenium halides III in the process of the invention in which all or nearly all of the radicals $T^1$, $T^2$, $T^3$, $T^4$, $T^5$, and $T^6$ are the same.

Of the class of phosphazenium halides of the general formula III, in which the substituents $T^1$, $T^2$, $T^3$, $T^4$, $T^5$, and $T^6$ stand for hydrocarbon substituents, it is preferred to use the phosphazenium halides of the formula IIIa

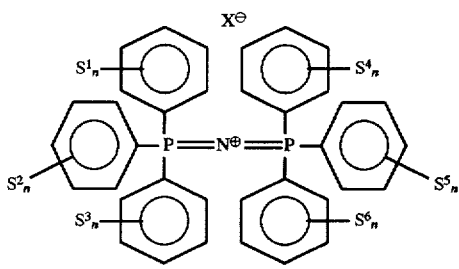

In this formula, X is the counterion to the positively charged nitrogen atom of the phosphazenium compound. X is generally a halide ion, for example, a chloride, bromide, or iodide ion. The individual phenyl rings of the phosphazenium compound IIIa can be unsubstituted or can carry from one to three, preferably one, of the relevant substituents $S^1$, $S^2$, $S^3$, $S^4$, $S^5$, or $S^6$. The substituents $S^1$, $S^2$, $S^3$, $S^4$, $S^5$, or $S^6$ can be the same or different and independently stand for $C_1$–$C_{20}$ alkyl, preferably $C_1$–$C_{10}$ alkyl, particularly $C_1$–$C_4$ alkyl groups, $C_1$–$C_{20}$ alkoxy, preferably $C_1$–$C_{10}$ alkoxy and more preferably $C_1$–$C_4$ alkoxy groups or halogen atoms, preferably chlorine or bromine atoms. This means that each individual ring of the six phenyl rings in the phosphazenium compound IIIa can be, independently of the degree of substitution and the substitution pattern of the other phenyl rings in the phosphazenium compound IIIa, either unsubstituted or can carry from one to three, preferably one, identical or different, preferably identical, substituent(s) of said substituents $S^1$, $S^2$, $S^3$, $S^4$, $S^5$, or $S^6$. The index n in formula IIIa designates the number of the relevant substituents $S^1$, $S^2$, $S^3$, $S^4$, $S^5$, or $S^6$ on the respective phenyl ring and consequently has a value of 0 if the relevant phenyl ring is unsubstituted, or an integral value of 1 to 3 if the relevant phenyl ring carries 1, 2, or 3 of said substituents $S^1$, $S^2$, $S^3$, $S^4$, $S^5$, or $S^6$. The substituents $S^1$, $S^2$, $S^3$, $S^4$, $S^5$, or $S^6$ are associated with the respective phenyl ring, ie. $S^1$ stands for the substituent(s) on phenyl ring 1, $S^2$ for the substituent(s) on phenyl ring 2, and so on.

The degree of substitution and the substitution pattern of the individual phenyl rings in the phosphazenium compounds IIIa containing the relevant substituents $S^1$, $S^2$, $S^3$, $S^4$, $S^5$, or $S^6$ generally has no crucial significance concerning the activity of the phosphazenium halides IIIa as co-catalyst in the catalyst system which is used in the present invention. For this reason it is preferred to use those phosphazenium halides IIIa in the process of the invention which can be prepared without much trouble. Examples for such phosphazenium halides IIIa are given below:

bis(tri-p-methylphenyl-phosphoranyli-dene)iminium halide ($S^1$–$S^6$ = 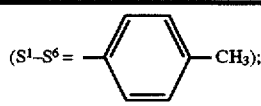 —CH₃);

bis(tri-p-chlorophenyl-phosphoranyli-dene)iminium halide ($S^1$–$S^6$ = 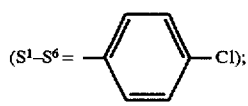 —Cl);

bis(tri-3,5-dichlorophenyl-phosphoranyli-dene)iminium halide ($S^1$–$S^6$ = 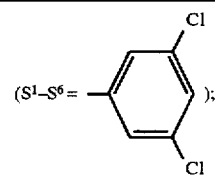 );

bis(tri-p-methoxyphenyl-phosphoranyli-dene)iminium halide ($S^1$–$S^6$ = 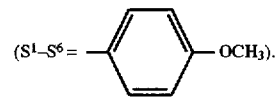 —OCH₃).

It is particularly preferred to used, in the process of the invention, the unsubstituted bis-triphenylphosphazenium halides of the formula IIIb

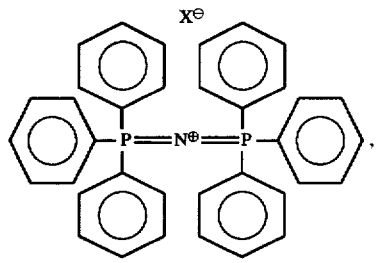 (IIIb)

in which X can be a chloride, bromide or iodide ion. It is, of course, possible to use mixtures of different phosphazenium halides of the general formula III in the process of the invention, but it is preferred to use one specific phosphazenium salt III.

The phosphazenium salts of the general formula IIIa and particularly IIIb have the advantage that they can be prepared cheaply from simple, readily available starting materials and in a very simple manner, eg. by the methods proposed by Martinsen et al, Acta Chem. Scand. Ser. A 31, 645 (1977), Kukushkin et al, Inorg. Chim. Acta176, 79 (1990), or Ruff et al, Inorganic Syntheses (ed. G.W. Parshall), Vol XV, pp 84 to 87 McGraw-Hill, New York 1974.

Of the class of the phosphazenium halides of the general formula III in which the substituents $T^1$, $T^2$, $T^3$, $T^4$, $T^5$, and $T^6$ stand for amino group substituents, the bis[tris(dialkylamino)] phosphazenium halides of the general formula IIIc

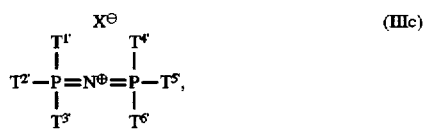 (IIIc)

are preferred in which the substituents $T^1$, $T^2$, $T^3$, $T^4$, $T^5$, and $T^6$ independently stand for the same or different, preferably the same, di-($C_1$–$C_4$ alkyl)amino groups or di-($C_3$–$C_6$ cycloalkyl)amino groups or for cyclic, amino group-containing substituents, in particular pyrrolidinyl, piperidinyl, morpholinyl, or N'-($_1$–$C_4$ alkyl)-piperazinyl groups and X is a chloride, bromide or iodide ion. As examples of particularly preferred phosphazenium halides of the class IIIc there may be mentioned:

Bis[tris(dimethylamino)phosphoranylidene]iminium halides;
bis[tris(N-pyrrolidinyl)phosphoranylidene]iminium halides;
bis[tris(N-piperidinyl)phosphoranylidene]iminium halides;
bis[tris(N-morpholinyl)phosphoranylidene]iminium halides;

bis[tris(N'-methyl)-N-piperazinyl)phosphoranylidene]
iminium halides;
bis[tris(dicyclopropylamino)phosphoranylidene]iminium
halides;
bis[tris(dicyclopentylamino)phosphoranylidene]iminium
halides;
bis[tris(dicyclohexylamino)phosphoranylidene]iminium
halides.

In the process of the invention there can be used, in place of, or supplementary to, the phosphazenium halides III, as co-catalysts, phosphazanium halides of the general formula IV

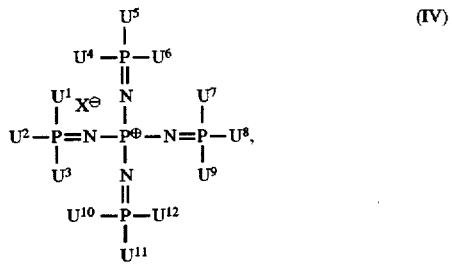

in which the substituents $U^1$, $U^2$, $U^3$, $U^4$, $U^5$, $U^6$, $U^7$, $U^8$, $U^9$, $U^{10}$, $U^{11}$, and $U^{12}$ are the same or different and independently stand for optionally substituted $C_1$–$C_{20}$ alkyl groups, optionally substituted $C_6$–$C_{10}$ aryl groups, optionally substituted $C_7$–$C_{12}$ aralkyl groups, di-($C_1$–$C_{10}$ alkyl)amino groups, di-($C_3$–$C_8$ cycloalkyl)amino groups, di-($C_6$–$C_{10}$ aryl)amino groups, ($C_1$–$C_{10}$-alky)amino and ($C_6$–$C_{10}$ aryl) amino groups, di-($C_7$–$C_{12}$ aralkyl)amino groups, ($C_1$–$C_{10}$-alkyl)amino and ($C_7$–$C_{12}$ aralkyl)amino groups, ($C_6$–$C_{10}$-aryl)amino and ($C_7$–$C_{12}$ aralkyl)amino groups, pyrrolidinyl, piperidinyl, morpholinyl, or N'-($C_1$–$C_4$ alkyl)piperazinyl groups. Preferred phosphazanium salts IV are those in which the substituents $U^1$, $U^2$, $U^3$, $U^4$, $U^5$, $U^6$, $U^7$, $U^8$, $U^9$, $U^{10}$, $U^{11}$, and $U^{12}$ independently stand for the same or different, preferably the same, di-($C_1$–$C_4$ alkyl)amino groups, di-($C_3$–$C_6$ cycloalkyl)amino groups or for cyclic amino groups, in particular pyrrolidinyl, piperidinyl, morpholinyl oder N'-($C_1$–$C_4$ alkyl)piperazinyl groups. In the phosphazanium halides IV, X is preferably a chloride, bromide, or iodide ion.

In the process of the invention the phosphazanium halides IV can be used alone or in mixtures containing the phosphazenium halides III as co-catalysts. Phosphazanium halides IV are preferably used alone, as co-catalysts.

The phosphazenium halides of the class depicted by formula IIIc und the phosphazanium halides IV can be prepared in a simple manner, for example, on the principle of unit construction using the appropriate building blocks and following the generally useful process proposed by Schwesinger et al, Angew. Chem. 99, 1212 (1987), Schwesinger et al, Angew. Chem. 103, 1376 (1991), and Schwesinger et al, Angew. Chem. 104, 864 (1992) and, Angew. Chem. 105, 1420 (1993 ).

The second component of the catalyst system to be used in the present invention comprises a Lewis acid. A series of such Lewis acids which are suitable for use as catalysts for the isomerization of epoxy butenes to produce 2,5-dihydrofurans in the liquid phase, is given in EP-A 412,366, WO 91/13882, WO 93/10111, and U.S. Pat. No. 5,238,889, for which reason these prior art Lewis acids are incorporated herein by reference, as examples. The Lewis acids used can be, eg, in particular, the Lewis acids usually employed in preparative organic chemistry, such as zinc, zirconium, titan, nickel, or tin halides. Although the Lewis acids are used in the process of the invention preferably in the form of their halides, the use of halogen-free Lewis acids, eg, dialkyltin oxides, is possible. The halogen-containing Lewis acids can be used both in the form of metal/halogen/element compounds, such as zinc chloride, zinc bromide, zinc iodide, and titanium tetrachloride and in the form of organometallic halides, such as trialkyltin halides or triaryltin halides, for example triphenyltin iodide, tributyltin iodide, or tri-n-octyltin iodide, or tetraalkylantimony halides or tetraarylantimony halides, such as tetraphenylstibonium iodide. The Lewis acids particularly preferred for use in the process of the invention are zinc chloride, zinc bromide, zinc iodide, triphenyltin iodide, tributyltin iodide, or tri-n-octyltin iodide. Mixtures of different Lewis acids can, of course, be used in the process of the invention.

It is usually found to be advantageous for the process of the invention when at least one component of the catalyst combination phosphazenium halide III and/or phosphazanium halide IV/Lewis acid is an iodide.

Alternatively, elementary iodine can be used in the process of the invention instead of the Lewis acid. Presumably the iodine acts as an electron acceptor in this case in a manner similar to the Lewis acids, but, since the fate of the iodine molecule in the course of the reaction has not been monitored, this remains a mere assumption and does not exclude some other reaction mechanism of the iodine.

The isomerization of the epoxy butenes II to the 2,5-dihydrofurans I with the aid of the catalyst system of the present invention is carried out advantageously in the presence of a solubilizing agent, which has the object of solubilizing the catalyst components phosphazenium halide III and/or phosphazanium halide IV and the Lewis acid, ie of promoting both the contact and the catalytic cooperation of these components with each other and the contact of these catalyst components with the reaction medium. By reaction medium is meant in particular in this case the epoxy butene II and mixtures thereof with the dihydrofuran I and optionally with oligomers and polymers of the epoxy butene II such as are formed in the course of the reaction. Thus suitable solubilizing agents are substances which are capable of dissolving the two catalyst components or of effecting incipient dissolution thereof and thus of improving the contact of the catalyst components with each other and with the reaction medium. Since, apart from the ability to solubilize the components of the catalyst system, phosphazenium halide III and/or phosphazanium halide IV and Lewis acid, and otherwise to be inert under the reaction conditions, ie to have no detrimental effect on the yield and selectivity of the reaction, theoretically no further demands need be made on the solubilizing agent with respect to its chemical properties, a large number of substances can be used as solubilizing agents. For example, there may be mentioned as solubilizing agents dipolar-aprotic solvents such as tetramethyl urea, cyclic ureas, such as N,N-dimethylethylene urea or N,N-dimethylpropylene urea, phosphoric acid triamides, such as hexamethylphosphoric acid triamide, N-alkylpyrrolidones, such as N-methylpyrrolidone, N-octylpyrrolidone, N-cyclohexylpyrrolidone, amides, such as N,N-dimethylformamide, N,N-dimethylacetamide, N,N-diethylacetamide, ethers, such as tetrahydrofuran, dioxane, dimethoxy ethane or, poly(ethylene glycol dialkyl ether)s, sulfoxides, such as dimethyl sulfoxide, or sulfones, such as dimethyl sulfone or sulfolane (tetrahydrothiophene-1,1-dioxide).

Of course, a number of the cited solubilizing agents can be added to the reaction batch consecutively or in the form of mixtures for solubilization of the catalyst components phosphazenium halide III and/or phosphazanium halide IV and Lewis acid. In addition, further solvents which are inert under the reaction conditions, such as diethyl ether, esters, such as ethyl acetate, ketones, such as acetone, or aromatic solvents, such as benzene, toluene, or xylene can also be added for dilution of the reaction mixture.

Since the amount of the solubilizing agent required for solubilization of the catalyst system phosphazenium halide III and/or phosphazanium halide IV/Lewis acid generally depends on the kind of Lewis acid used and on the solubilizing agent itself, it is recommendable to determine, in each case, the optimum amount of solubilization agent to be added in a simple trial run.

Since the phosphazenium halides III and the phosphazanium halides IV are inherently soluble to a certain extent in the organic reaction medium of the process, ie, in the epoxy butene II itself and in the mixtures of epoxy butene II, 2,5-dihydrofuran I, and epoxybutene oligomers and polymers formed as a consequence of the reaction, and some of the Lewis acids, in particular organometallic Lewis acids, such as dialkyltin oxides, trialkyltin halides, or triaryltinhalides or tetraalkylstibonium halides, likewise show a certain degree of solubility in this reaction medium, the solubility of the catalyst system in the organic reaction medium can be so great that the addition of a solubilizing agent to the reaction batch is unnecessary. This particularly applies if lipophilic phosphazenium halides and/or lipophilic phosphazanium halides IV are used, and together with them lipophilic phosphazenium halides III and/or lipophilic phosphazanium halides IV, organometallic Lewis acids which are soluble in the organic reaction medium, such as those mentioned above, are used as catalyst system. If desired a mixture of epoxy butene II with the reactionsproduct 2,5-dihydrofuran and the epoxy-butene oligomers and polymers formed in the course of the reaction can be used from the outset of the reaction.

The catalyst components phosphazenium halide III and/or phosphazanium halide IV/Lewis acid are usually placed in the reactor in the presence or absence of the solubilizing agent for carrying out the reaction and the epoxy butene II to be converted is pumped into this mixture. This order of addition is not obligatory however and can be changed as desired. The solubilizing agent is advantageously added to the reaction mixture in such quantities that a major part of the catalyst system phosphazenium halide III and/or phosphazanium halide IV/Lewis acid passes into solution.

The process of the invention can be carried out batchwise, eg, in stirred boilers, or continuously, eg, in cascade reactors, tubular reactors, or loop reactors.

When the process is carried out batchwise, the phosphazenium halide III and/or phosphazanium halide IV is usually employed, based on butadiene epoxide II used, in amounts of from 0.01 to 5 wt %, preferably of from 0.5 to 1 wt %, and the Lewis acid in amounts of from 0.02 to 10 wt %, preferably of from 0.5 to 2 wt %.

Since the catalyst system of the invention acts purely catalytically, ie remains virtually unconsumed during isomerization of the epoxy butene II to the 2,5-dihydrofuran I, the above concentration data are to be regarded only as guide values for the batch process.

Accordingly, when the process is carried out continuously, generally a specific amount of the catalyst system is placed in the reactor, the epoxy butene is passed in continuously and the 2,5-dihydrofuran is removed from the reaction mixture constantly at the rate at which it is formed, for example, by distillation, and passed on for further utilization. When use is made of tubular reactors in the continuous process, the solution of the catalyst system in the solubilizing agent obtained following separation of 2,5-dihydrofuran product is advantageously returned to the reactor, ie, the catalyst solution is recycled. Alternatively, a partial stream of the catalyst solution can be recycled. Analogously to the continuous process, the catalyst solution remaining following separation of 2,5-dihydrofuran in the batch process can be used again for catalyzing the epoxybutene isomerization reaction.

The phosphazenium halide III and/or the phosphazanium halide IV is/are generally added, in respect of the Lewis acid, in a ratio, by weight, of phosphazenium halide III and/or phosphazanium halide IV to Lewis acid ranging from 1:0.01 to 1:10, preferably ranging from 1:0.02 to 1:2.

The process of the invention is generally carried out at temperatures of from 60° to 200° C., preferably at a temperature of from 90° to 180° C. Depending on the type and quantity of the catalyst system used and depending on the temperature of reaction, reaction times are generally required of from a few minutes to 24 h for a complete reaction.

The process of the invention is generally carried out at atmospheric pressure. It is also possible to carry out the process under reduced pressure or under elevated pressure, in particular under autogenous pressure.

A particular advantage of the process of the invention resides in the fact that the phosphazenium halides III and the phosphazanium halides IV can be readily separated from oligomeric and polymeric by-products which accumulate in the catalyst mixture during prolonged operation, by causing the phosphazenium halides III or phosphazanium halides IV to crystallize out from the catalyst mixture by cooling the mixture, followed by filtration to isolate the crystals. The crystallization can be stimulated by the addition of a solvent such as toluene, methanol, ethanol, acetone, or ethyl acetate. The phosphazenium halides III or phosphazanium halides IV recovered in this manner can then be used again as catalyst component. This regeneration of the catalyst solution can take place batchwise or continuously, for example, by tapping off a partial stream from the catalyst solution to be recycled for the purpose of regeneration, regenerating it in the above manner and then recycling it to the reaction.

On account of the high efficiency of the phosphazenium halides III and the phosphazanium halides IV as co-catalysts generally smaller amounts of these catalyst components are required to achieve the same results in the isomerization of epoxy butenes II to 2,5-dihydrofurans I than when use is made of alkali metal, ammonium, or phosphonium halides, which have hitherto been used for this purpose. Similarly the content of the Lewis acid can be lowered on account of the high efficiency of the phosphazenium halides III and the phosphazanium halides IV in the catalyst system of the invention. For example, good results can be achieved when using a Lewis-acid content of as little as 5 mol % in the catalyst system, based on the phosphazenium halide IIIb.

Another advantage is that particularly cheap Lewis acids, such as zinc halides, combined with the phosphazenium halides III and with the phosphazanium halides IV, have very good selectivities in the process of the invention, so that the use of more expensive, organometallic Lewis acids, such as organotin halides, which are usually used to increase the selectivity of the reaction in combination with phosphonium iodides, is not absolutely necessary.

The epoxy butenes II required as starting materials can be obtained, for example, by the method proposed by Kadesch (J. Am Chem. Soc. 68, 41 (1946)) or by the process described in U.S. Pat. No. 4,897,498 and U.S. Pat. No. 4,950,773.

The 2,5-dihydrofurans I which can be produced in the process of the invention can be hydrogenated by usual methods to form the corresponding tetrahydrofurans, which serve as solvents and as monomers for the preparation of polytetrahydrofurans.

EXAMPLES

Example 1

The following mixture was placed in a stirred flask having a capacity of 250 mL and heated to 130° C., 10 g of bis(triphenylphosphoranyliden)iminium iodide (IIIb),
0.7 g of zinc iodide and
60 g of N-cyclohexylpyrrolidone.

32 g of vinyl oxirane (epoxy butene) were metered in per hour using a variable-flow pump. At the same time, a mixture of 2,5-dihydrofuran and unconverted vinyl oxirane distilled off.

Following a period of 10 h, the amount of vinyl oxirane pumped in is 320 g and that of distillate obtained is 300 g. After reduction of the pressure to 10 mbar a further 14 g of distillate were obtained. GC-analysis showed that the combined distillates had the following composition,
84 wt % of 2,5-dihydrofuran
15.7 wt % of vinyl oxirane
0.3 wt % of crotonaldehyde.

At a conversion rate of 84.6% a selectivity of 97.4% was achieved.

The distillate was then passed through the catalyst solution at the same rate for a second time, and on completion of the feed the pressure was reduced again.

308 g of distillate were thus obtained having the following composition:
97.7 wt % of 2,5-dihydrofuran
2 wt % of vinyl oxirane
0.3 wt % of crotonaldehyde.

The overall selectivity over both stages was 96% at a conversion of 98%.

The liquid distillation residues remaining following the removal, by distillation, of the low-boiling fractions were admixed with 90 mL of ethyl acetate to cause precipitation of solids. Following a period of 6 h the solids were removed by filtration, and the crystals obtained were washed with ethyl acetate and then dried under reduced pressure to remove the solvent. The dried solids were weighed and chemically analyzed. They consisted of a mixture of 0.6 g of zinc iodide with 9 g of bis(triphenylphosphoranylidene) iminium iodide. This mixture could be used again as catalyst in the reaction.

Example 2

32.3 g of bis(triphenylphosphoranylidene)iminium iodide, 21 g of triphenyltin iodide, and 60 g of poly(ethylene glycol dimethyl ether) ($\overline{M}_w$ 2000) were heated in a stirred flask to 105° C. Over a period of 10 h, 510 g of vinyl oxirane were added at a steady rate and the low-boiling fractions were concurrently removed by distillation. On completion of the feed the pressure was reduced to 10 mbar.

There were obtained 507 g of distillate having the following composition:
0.1 wt % of vinyl oxirane
8.9 wt % dihydrofuran and
1 wt % of crotonaldehyde.

A selectivity of 98% at a conversion of 80% can be calculated from these findings.

Example 3

In a stirred flask having a capacity of 250 mL there was placed the following mixture, which was then heated to 130° C.:

10 g of tetrakis[tris(dimethylamino)phorphoranylideneimino]phosphazanium iodide to of the formula

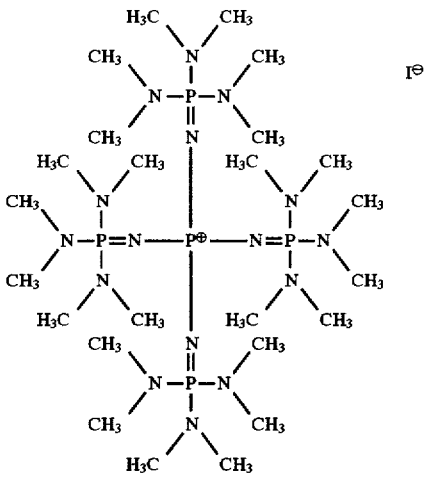

0.55 g of zinc iodide, and
47 g of N-cyclohexylpyrrolidone.

Over a period of 10 h, 400 g of vinyl oxirane were added and the low-boiling fractions were removed concurrently by distillation. On completion of the feed the pressure was reduced to 10 mbar.

There were obtained 390 g of distillate having the following composition:
28 wt % of vinyl oxirane,
71.5 wt % of 2,5-dihydrofuran and
0.5 wt % of crotonaldehyde.

A selectivity of 96% and a conversion of 73% can be calculated from these findings.

Example 4

In a stirred flask having a capacity of 250 mL there was placed the following mixture, which was then heated to 130° C.:

7 g of bis[tris(dimethylamino)phorphoranylidene]iminium iodide of the formula

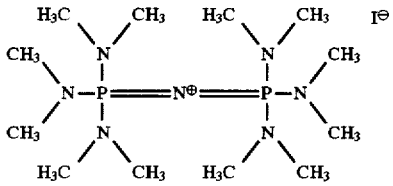

0.7 g of zinc iodide, and
60 g of N-cyclohexylpyrrolidone.

Over a period of 10 h, 510 g of vinyl oxirane were added and the low-boiling fractions were removed concurrently by distillation. On completion of the feed the pressure was reduced to 10 mbar.

There were obtained 500 g of distillate having the following composition:
18 wt % of vinyl oxirane,
81.6 wt % of 2,5-dihydrofuran and 0.4 wt % of crotonaldehyde.

A selectivity of 98% and a conversion of 82% can be calculated from these findings.

I claim:

1. A process for the preparation of a 2,5-dihydrofuran of the general formula I

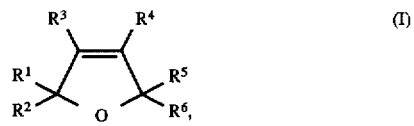

in which the radicals $R^1$, $R^2$, $R^3$, $R^4$, $R^5$, and $R^6$ are the same or different and stand for hydrogen or $C_1$–$C_4$ alkyl groups, by the catalytic rearrangement of 3,4-epoxy-1-butenes of the general formula II

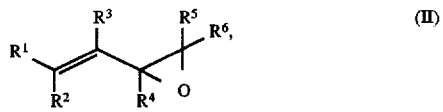

in the presence of a Lewis acid or elementary iodine and in the presence or absence of an organic solubilizing agent at a temperature of from 60° to 200° C., wherein the reaction is carried out in the presence of a phosphazenium halide or a phosphazanium halide or in the presence of mixtures of phosphazenium and phosphazanium halides.

2. A process as defined in claim 1, wherein the reaction is carried out in the presence of a phosphazenium halide of the general formula III

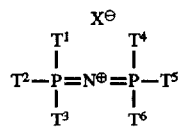

in which X denotes a chloride, bromide or iodide ion and in which the substituents $T^1$, $T^2$, $T^3$, $T^4$, $T^5$, and $T^6$ are the same or different and independently stand for optionally substituted $C_1$–$C_{20}$ alkyl groups, optionally substituted $C_6$–$C_{10}$ aryl groups, optionally substituted $C_7$–$C_{12}$aralkyl groups, di-($C_1$–$C_{10}$ alkyl) amino groups, di-($C_3$–$C_8$ cycloalkyl) amino groups, di-($C_6$–$C_{10}$ aryl)amino groups, ($C_1$–$C_{10}$ alkyl)amino and ($C_6$–$C_{10}$ aryl)amino groups, di-($C_7$–$C_{12}$ aralkyl)amino groups, ($C_1$–$C_{10}$ alkyl)amino and ($C_7$–$C_{12}$ aralkyl)amino groups, ($C_6$–$C_{10}$ aryl)amino and ($C_7$–$C_{12}$ aralkyl)amino groups, pyrrolidinyl, piperidinyl, morpholinyl oder N'-($C_1$–$C_4$ alkyl)piperazinyl groups.

3. A process as defined in claim 1, wherein the reaction is carried out in the presence of a phosphazenium halide of the general formula IIIa

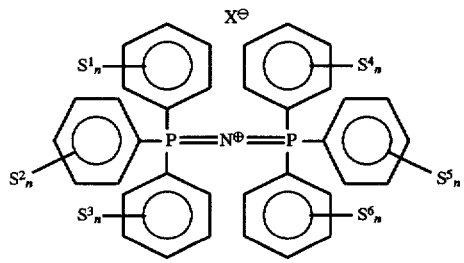

in which X stands for a chloride, bromide or iodide ion and each of the six phenyl rings of the phosphazenium halide IIIa is either unsubstituted or carries from 1 to 3 identical or different relevant substituents $S^1$, $S^2$, $S^3$, $S^4$, $S^5$, or $S^6$, where $S^1$, $S^2$, $S^3$, $S^4$, $S^5$, or $S^6$ denote $C_1$–$C_{20}$ alkyl groups, $C_1$–$C_{20}$ alkoxy groups, chlorine and/or bromine and, designates the number of relevant substituents $S^1$, $S^2$, $S^3$, $S^4$, $S^5$, or $S^6$ on the respective phenyl ring and has an integral value of 0 to 3.

4. A process as defined in claim 1, wherein the reaction is carried out in the presence of a phosphazenium halide of the formula IIIb

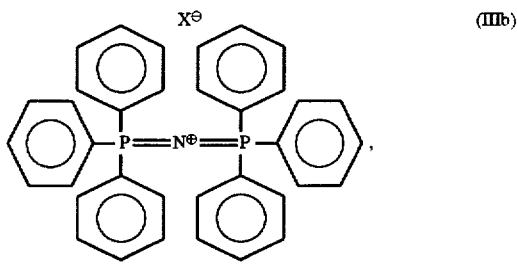

in which X stands for a chloride, bromide or iodide ion.

5. A process as defined in claim 1, wherein the reaction is carried out in the presence of a phosphazenium halide of the formula IIIc

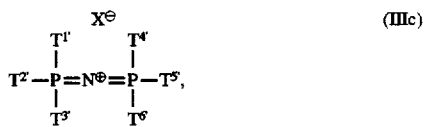

in which the radicals $T^{1'}$, $T^{2'}$, $T^{3'}$, $T^{4'}$, $T^{5'}$ and $T^{6'}$ are the same or different and independently stand for di-($C_1$–$C_4$ alkyl) amino groups or for pyrrolidinyl, piperidinyl, morpholinyl or N'-($C_1$–$C_4$ alkyl)piperazinyl groups and X is a chloride, bromide or iodide ion.

6. A process as defined in claim 1, wherein the reaction is carried out in the presence of a phosphazanium halide of the formula IV

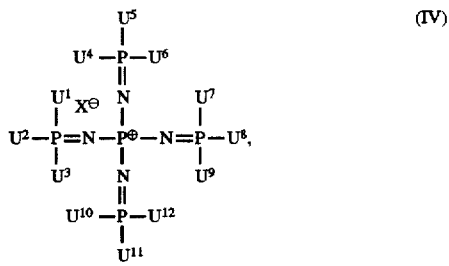

in which the substituents $U^1$, $U^2$, $U^3$, $U^4$, $U^5$, $U^6$, $U^7$, $U^8$, $U^9$, $U^{10}$, $U^{11}$, and U are the same or different and independently stand for optionally substituted $C_1$–$C_{20}$ alkyl groups, optionally substituted $C_6$–$C_{10}$ aryl groups, optionally substituted $C_7$–$C_{12}$ aralkyl groups, di-($C_1$–$C_{10}$ alkyl)amino groups, di-($C_3$–$C_8$ cycloalkyl)amino groups, di-($C_6$–$C_{10}$ aryl)amino groups, ($C_1$–$C_{10}$ alkyl)amino and ($C_7$–$C_{12}$ aralkyl)amino groups, ($C_6$–$C_{10}$ aryl)amino and ($C_7C_{12}$ aralkyl)amino groupa, pyrrolidinyl, piperidinyl, morpholinyl or N'-($C_1$–$C_4$ alkyl)piperazinyl groups.

7. A process as defined in claim 1, wherein the reaction is carried out in the presence of a phosphazanium halide of the formula IV, in which the substituents $U^1$, $U^2$, $U^3$, $U^4$, $U^5$, $U^6$, $U^7$, $U^8$, $U^9$, $U^{10}$, $U^{11}$, and $U^{12}$ are the same or different and independently stand for di-($C_1$–$C_4$alkyl)amino groups, pyrrolidinyl, piperidinyl, morpholinyl oder N'-($C_1$–$C_4$ alkyl) piperazinyl groups and X is a chloride, bromide or iodide ion.

8. A process as defined in claim 1, wherein the phosphazenium and/or phosphazanium halides of the general formulas III and IV are used, relatively to the Lewis acid, in a ratio, by weight, of phosphazenium halide III and/or phosphazanium halide IV to Lewis acid ranging from 1:0.01 to 1:10 einsetzt.

9. A process as defined in any of claim 1, wherein at least one of the components of the catalyst system phosphazenium halide III and/or phosphazanium halide IV/Lewis acid is an iodide.

10. A process as defined in any of claim 1, which is carried out in the presence of a solubilizing agent.

11. A process as defined in any of claim 1, which is carried out in the absence of a solubilizing agent.

12. A process as defined in any of claim 1, wherein a zinc halide is used as Lewis acid.

13. A process as defined in any of claim 1, wherein an organometallic is used as Lewis acid.

14. A continuous embodiment of the process as defined in claim 1, wherein an epoxy butene of the general formula II is added to a mixture of a phosphazenium halide or phosphazanium halide or of phosphazenium halide/phosphazanium halide mixtures containing a Lewis acid in the presence or absence of an organic solubilizing agent at the temperature of reaction and the dihydrofuran I formed during the reaction is continuously removed during the reaction by distillation.

15. A process as defined in any of claim 1, wherein the epoxy butene II used is vinyl oxirane of the formula IIa.

16. A process as defined in claim 2, wherein the reaction is carried out in the presence of a phosphazenium halide of the general formula III

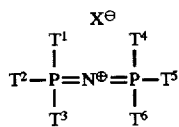

in which X denotes a chloride, bromide or iodide ion and in which the substituents $T^1$, $T^2$, $T^3$, $T^4$, $T^5$, and $T^6$, are the same or different and independently stand for optionally substituted $C_1$–$C_{20}$ alkyl groups, optionally substituted $C_6$–$C_{10}$ aryl groups optionally substituted $C_7$–$C_{12}$ aralkyl groups, di-($C_1$–$C_{10}$-alkyl) amino groups, di-($C_3$–$C_8$ cycloalkyl)amino groups, di-$C_6$–$C_{10}$ aryl)amino groups, ($C_1$–$C_{10}$-alkyl) amino and ($C_6$–$C_{10}$ aryl)amino groups, di-($C_7$–$C_{12}$-aralkyl) amino groups, ($C_1$–$C_{10}$-alkyl)amino and ($C_7$–$C_{12}$ aralkyl(amino groups, ($C_6$–$C_{10}$ aryl)amino and ($C_7$–$C_{12}$ aralkyl)amino groups, pyrrolidinyl, piperidinyl, morpholinyl oder N'-($C_1$–$C_4$ alkyl)piper-azinyl groups.

17. A process as defined in claim 2, wherein the reaction is carried out in the presence of a phosphazenium halide of the formula IIIc

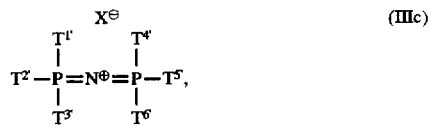

in which the radicals $T^{1'}$, $T^{2'}$, $T^{3'}$, $T^{4'}$, $T^{5'}$, and $T^{6'}$ are different and independently stand for di-($C_1$–$C_4$ alkyl)amino groups or for pyrrolidinyl, piperidinyl, morphonlinyl of N'-($C_1$–$C_4$ alkyl)piperazinyl groups and X is a chloride, bromide or iodide ion.

18. A process as defined in claim 6, wherein the reaction is carried out in the presence of a phosphazanium halide of the formula IV,

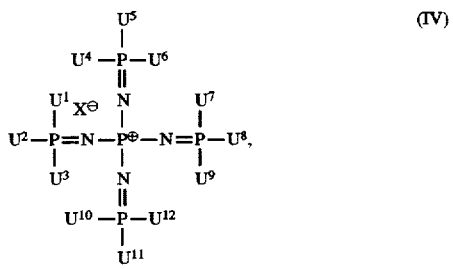

in which the substituents $U^1$, $U^2$, $U^3$, $U^4$, $U^5$, $U^6$, $U^7$, $U^8$, $U^9$, $U^{10}$, $U^{11}$, $U^{12}$, are the same or different and independently stand for optionally substituted $C_1$–$C_{20}$ alkyl groups, optionally substituted $C_6$–$C_{10}$ aryl groups, optionally substituted $C_7$–$C_{12}$ aralkyl groups, di-($C_1$–$C_{10}$ alkyl)amino groups, di-($C_3$–$C_8$ cycloalkyl)amino groups, di-($C_6$–$C_{10}$-aryl) amino groups, ($C_1$–$C_{10}$ alkyl)amino and $C_6$–$C_{10}$ aryl)amino groups, di-($C_7$–$C_{12}$ aralkyl)amino groups, ($C_1$–$C_{10}$ alky) amino and ($C_6$–$C_{10}$ aryl)amino and $C_7$–$C_{12}$ aralkyl)amino groups, pyrrolidinyl, piperidinyl, morpholinyl or N'-($C_1$–$C_4$ alkyl)piperazinyl groups.

* * * * *

UNITED STATES PATENT AND TRADEMARK OFFICE
CERTIFICATE OF CORRECTION

PATENT NO.: 5,627,291

DATED: May 6, 1997

INVENTOR(S): FISCHER, Martin

It is certified that error appears in the above-identified patent and that said Letters Patent is hereby corrected as shown below:

In the Abstract, line 1, "A proces" should be --A process--.

Column 13, claim 2, line 49, "oder" should be --or--.

Column 14, claim 7, line 65, "oder" should be --or--.

Column 16, claim 16, line 4, "oder" should be --or--.

Column 14, claim 3, line 3, "and, designates" should be --and n designates--.

Column 14, claim 6, line 51, "U" should be $-- U^{12} --$.

Column 15, claim 8, line 6, delete "einsetzt".

Column 16, claim 18, line 41, "alky" should be --alkyl--.

Signed and Sealed this

Fifth Day of August, 1997

Attest:

Attesting Officer

BRUCE LEHMAN

Commissioner of Patents and Trademarks